(12) United States Patent
Uttarwar et al.

(10) Patent No.: US 7,511,161 B2
(45) Date of Patent: Mar. 31, 2009

(54) PROCESS FOR THE PURIFICATION OF CITALOPRAM

(75) Inventors: Sunil Govindrao Uttarwar, Maharashtra (IN); Bhagwan Narayan Gawli, Maharashtra (IN)

(73) Assignee: Meditab Specialities Pvt. Ltd., Mumbai (IN)

( * ) Notice: Subject to any disclaimer, the term of this patent is extended or adjusted under 35 U.S.C. 154(b) by 47 days.

(21) Appl. No.: 10/565,736

(22) PCT Filed: Jul. 23, 2004

(86) PCT No.: PCT/GB2004/003209

§ 371 (c)(1), (2), (4) Date: Apr. 19, 2006

(87) PCT Pub. No.: WO2005/012278

PCT Pub. Date: Feb. 10, 2005

(65) Prior Publication Data

US 2006/0189816 A1    Aug. 24, 2006

(30) Foreign Application Priority Data

Jul. 25, 2003    (GB)    ................................. 0317475.2

(51) Int. Cl.
*C07D 307/00*    (2006.01)
(52) U.S. Cl. ..................................... 549/467
(58) Field of Classification Search ................ 549/467
See application file for complete search history.

(56) References Cited

U.S. PATENT DOCUMENTS 4,136,193 A    1/1979    Bogeso 6,635,773 B2 *    10/2003    Coppi et al.    ................. 549/467

FOREIGN PATENT DOCUMENTS

| CH | 691477 | | 7/2001 |
|---|---|---|---|
| EP | 1288211 | | 3/2003 |
| GB | 2375763 | * | 2/2002 |
| GB | 2375763 | | 11/2002 |
| WO | 0168627 | | 9/2001 |
| WO | 03057133 | | 7/2003 |
| WO | 2004 016602 | | 2/2004 |
| WO | 2005 012278 | | 2/2005 |

OTHER PUBLICATIONS

Search Report.

* cited by examiner

*Primary Examiner*—D. Margaret Seaman
*Assistant Examiner*—Nizal S Chandrakumar
(74) *Attorney, Agent, or Firm*—Novak, Druce & Quigg LLP

(57) ABSTRACT

A process of purifying citalopram, either in racemic or enantiomeric form, which process comprises (i) providing a crude mixture comprising citalopram, either in racemic or enantiomeric form, dissolved in a water immiscible organic solvent, and which mixture also includes one or more citalopram derivatives which are present as citalopram impurities; (ii) washing the crude mixture with at least one dilute aqueous solution of a polybasic acid, either in free form or as a partial alkali metal salt, so as to separate citalopram from citalopram impurities present in the crude mixture; and (iii) where required converting citalopram free base, separated from citalopram impurities further to step (ii), to a pharmaceutically acceptable salt.

29 Claims, No Drawings

PROCESS FOR THE PURIFICATION OF CITALOPRAM

This application is a 35 USC § 371 U.S. National Stage Application of International Application No. PCT/GB2004/003209, filed on Jul. 23, 2004, claiming the priority of Great Britain Application No. 0317475.2, filed Jul. 25, 2003, the entire disclosures of which are incorporated herein by reference in their entireties.

The present invention relates to purification of citalopram, citalopram prepared further to such purification and pharmaceutical formulations comprising the same.

Citalopram, 1-[3-(Dimethylamino)-propyl]-1-(4-fluorophenyl)-1,3-dizohydro-5-isobenzoftirancarbonitirile, has the following structural formula (I)

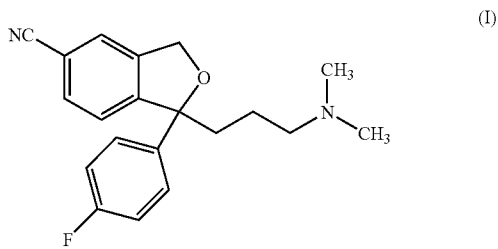

Citalopram is a selective, centrally acting serotonin (5-hydroxytryptamine; 5-HT) reuptake inhibitor, accordingly having antidepressant activities. The antidepressant activity of the compound has been reported in several publications, e.g. J. Hyttel, Neuro-Psychopharmacol. & Biol. Psychiat., 1982, 6, 277-295 and A. Gravem, Acta Psychiatr. Scand., 1987, 75, 478-486. Citalopram has further been disclosed to show effects in the treatment of dementia and cerebrovascular disorders, for example EP 474580B.

Citalopram was first disclosed in U.S. Pat. No. 4,136,193, which describes conversion of 5-bromo substituted phthalanes to the corresponding 5-cyano compound, using cuprous cyanide in a solvent such as dimethyl formamide, at elevated temperatures. The citalopram product obtained by such process is not, however, viable for use in pharmaceutical dosage forms since it contains impurities such as 5-carboxamide citalopram, desmethyl citalopram, chloro citalopram and bromo citalopram. Purification of citalopram thus obtained by such a process has been described by various methods.

For example, EP 1169314B describes crystallization of the free base of citalopram to remove the impurities. GB 2375763A describes a process of purification by formation of citalopram salts, such as the oxalate, and repeated basification and salt formation and manipulation of pH for removing selected impurities. EP 1288211A describes a similar process of purification of the hydrobromide by extraction at a pH in the range of 2 to 6. A process for purification by thin-film distillation is also described in GB 2356199B.

All the above referred to prior art processes suffer from a major disadvantage, in that the purification process has to be repeated a number of times, or it is necessary to be employed in conjunction with other methods to obtain citalopram of acceptable pharmaceutical grade. The processes are lengthy, tedious and not suitable for industrial scale manufacture of citalopram.

Citalopram and its impurities have different basicity. In the descending order of basicity, citalopram and its impurities are as follows:

5-carboxamide citalopram,
N-desmethyl citalopram,
desfluoro citalopram,
4[4-(dimethylamino)-1-(4'-fluorophenyl)-1-hydroxybutyl]-3-(hydroxymethyl)-benzonitrile [5-cyano diol],
5-formyl citalopram,
citalopram,
descyano citalopram,
5-chloro citalopram,
5-bromo citalopram.

In particular, some of the above listed impurities such as the cyano diol, desfluoro citalopram and 5-carboxamide citalopram in their enantiomeric form are likely impurities in the synthesis of escitalopram.

The structures of these impurities are as follows.

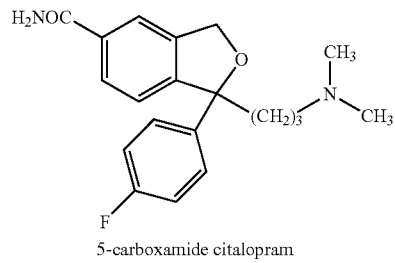
5-carboxamide citalopram

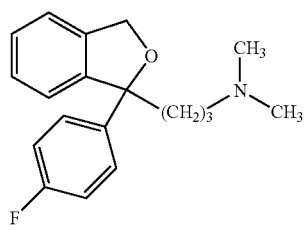
descyano citalopram

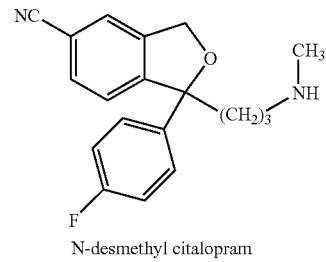
N-desmethyl citalopram

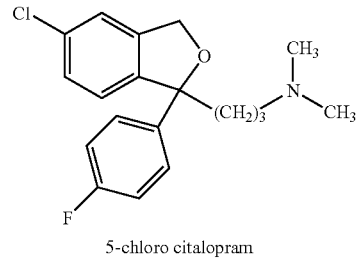
5-chloro citalopram

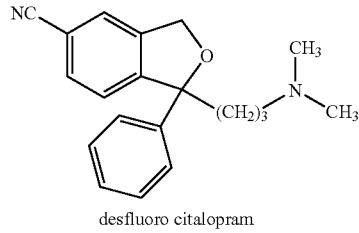
desfluoro citalopram

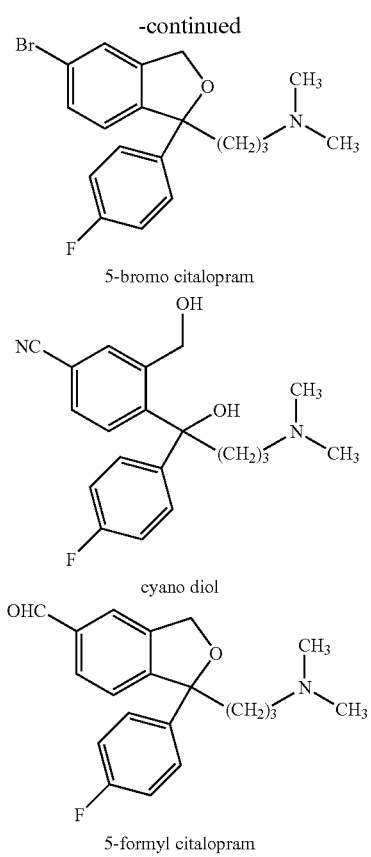

5-bromo citalopram cyano diol 5-formyl citalopram

The present invention describes a simple and novel process for the large-scale manufacture and purification of citalopram, escitalopram and their pharmaceutically acceptable salts without tedious and time-consuming disadvantages associated with prior art processes. More particularly, the present invention employs certain polybasic acids either in free form or as partial alkali metal salts having the capability of forming salts selectively with the impurities of citalopram and citalopram itself. This property of the polybasic acids either in free form or as partial alkali metal salts has advantageously been utilized by the present invention to purify citalopram or its enantiomers.

More particularly, there is provided by the present invention a process of purifying citalopram, either in racemic or enantiomeric form, which process comprises:

(i) providing a crude mixture comprising citalopram, either in racemic or enantiomeric form, dissolved in a water immiscible organic solvent, and which mixture also includes one or more citalopram derivatives which are present as citalopram impurities;

(ii) washing said crude mixture with at least one dilute aqueous solution of a polybasic acid, either in free form or as a partial alkali metal salt, so as to separate said citalopram from citalopram impurities present in said crude mixture; and (iii) where required converting citalopram free base, separated from citalopram impurities further to step (ii), to a pharmaceutically acceptable salt.

In a preferred embodiment, a process according to the present invention comprises initial washing of the crude mixture with at least one dilute aqueous solution of a polybasic acid, either in free form or as a partial alkali metal salt, so as to remove citalopram impurities from the crude mixture, and subsequently washing the residual crude mixture with at least one further dilute aqueous solution of a polybasic acid, either in free form or as a partial alkali metal salt, so as to separate citalopram, either in racemic or enantiomeric form, from the impurities remaining in the crude mixture, by extraction of citalopram, as a salt formed with the polybasic acid, into an aqueous phase. The thus obtained aqueous extraction phase now contains citalopram as a salt of the polybasic acid, to which can subsequently be added a base, such as an alkali metal hydroxide, such as sodium or potassium hydroxide, in an amount sufficient to liberate citalopram free base and extracting the liberated citalopram into an organic solvent.

According to the above described preferred embodiment of the present invention, there is provided a process of purifying citalopram, either in racemic or enantiomeric form, which process comprises:

(i) providing a crude mixture comprising citalopram, either in racemic or enantiomeric form, dissolved in a water immiscible organic solvent, and which mixture also includes one or more citalopram derivatives which are present as citalopram impurities;

(ii) washing said crude mixture with at least one dilute aqueous solution of a polybasic acid, either in free form or as a partial alkali metal salt, so as to remove citalopram impurities from the crude mixture;

(iii) washing the residual crude mixture obtained further to step (ii) with at least one further dilute aqueous solution of a polybasic acid, either in free form or as a partial alkali metal salt, so as to separate said citalopram from impurities remaining in said residual crude mixture, by extraction of citalopram, as a salt formed with the polybasic acid, into an aqueous phase and optionally washing the resulting aqueous phase with an organic solvent;

(iv) adding a base to the aqueous phase in an amount sufficient to liberate citalopram free base and extracting the liberated citalopram into an organic solvent;

(v) optionally re-extracting citalopram free base from the organic extract obtained further to step (iv) by washing with at least one further dilute aqueous solution of a polybasic acid, either in free form or as a partial alkali metal salt, so as to extract citalopram, as a salt formed with the polybasic acid, into an aqueous phase and adding thereto a base in an amount sufficient to liberate citalopram free base and further extracting the liberated citalopram into an organic solvent; and (vi) where required converting the free base obtained further to step (iv) or (v) to a pharmaceutically acceptable salt thereof.

Typically, the water immiscible solvent employed in step (i) as defined above can be selected from the group consisting of toluene, ethyl acetate, hexane and methylene dichloride. Preferably the water immiscible solvent is toluene or ethyl acetate.

Typically the polybasic acid is selected from the group consisting of tartaric acid, oxalic acid, fumaric acid, citric acid and edetic acid, which can either be employed in free form, or as a partial alkali metal salt. A suitable alkali metal salt is the sodium salt. A preferred polybasic acid is edetic acid, which can if required be preferably employed as disodium edetate.

The initial stage of washing the crude mixture with at least one dilute aqueous solution of a polybasic acid, either in free form or as a partial alkali metal salt, suitably removes impurities from the crude mixture having higher basicity compared to citalopram. Typically, therefore, the initial washing with at least one dilute aqueous solution of a polybasic acid, either in free form or as a partial alkali metal salt, can remove the following impurities if present in the crude mixture: 5-carboxamide citalopram, N-desmethyl citalopram, desfluoro citalopram, 4[4-(dimethylamino)-1-(4'-fluorophenyl) -1-hydroxybutyl]-3-(hydroxymethyl)-benzonitrile and/or 5-formyl citalopram. Typically, the strength of a dilute aqueous solution of a polybasic acid, either in free form, or as a partial alkali metal salt, as employed in the initial washing stage of a process according to the present invention is in the range of 0.5% to 6%.

Further to removal of the above referred to impurities from the crude mixture, the residual organic crude mixture comprises citalopram, either in racemic or enantiomeric form, together with impurities less basic than citalopram. A subsequent washing stage so as to separate citalopram, either in racemic or enantiomeric form, from the thus residual crude mixture, comprises washing the residual crude mixture containing citalopram, either in racemic or enantiomeric form, with at least one further dilute aqueous solution of a polybasic acid, either in free form or as a partial alkali metal salt, whereby citalopram as a salt formed with the polybasic acid is extracted into an aqueous phase. This extraction is normally done at ambient temperature, but can be done equally effectively at elevated temperatures, such as 40 to 80° C. It will be appreciated, therefore, that residual impurities having a basicity of less than citalopram, such as for example, descyano citalopram, 5-chloro citalopram and/or 5-bromo citalopram, are retained in the organic phase. Typically, the strength of a dilute aqueous solution of a polybasic acid, either in free form, or as a partial alkali metal salt, as employed in the subsequent washing stage of a process according to the present invention, is in the range of 4% to 25%.

The resulting aqueous phase now contains citalopram, either in racemic or enantiomeric form, as a salt with the polybasic acid. The aqueous phase can also be further purified by washing with an organic solvent as indicated above, such as toluene, ethyl acetate, hexane, methylene dichloride, or the like. During this washing of the aqueous phase with an organic solvent, such as toluene, it may be desirable for the aqueous phase to be further strengthened by adding small amounts of polybasic acid prior to the organic wash, as this can be more effective and loss of citalopram into the organic phase can be reduced.

A process according to the present invention preferably further comprises adding a base to the aqueous phase in an amount sufficient to liberate citalopram free base, and suitably the base comprises an aqueous alkali metal hydroxide solution, such as aqueous sodium hydroxide or potassium hydroxide. Typically, the liberated citalopram free base is then extracted from the aqueous phase into a water immiscible solvent, such as ethyl acetate. It may be desirable as indicated above to carry out a re-extraction process of the citalopram free base present in the resulting organic extract, by washing with at least one further dilute aqueous solution of a polybasic acid, either in free form or as a partial alkali metal salt, so as to extract citalopram, as a salt formed with the polybasic acid, into an aqueous phase and again adding thereto a base in an amount sufficient to liberate citalopram free base and further extracting the liberated citalopram into an organic solvent. This re-extraction process can also help to remove less basic citalopram impurities.

The resulting citalopram free base can where required be converted to a pharmaceutically acceptable salt of citalopram, such as the hydrobromide, hydrochloride or oxalate. The pharmaceutically acceptable salts of citalopram, such as the hydrobromide, hydrochloride or oxalate, may be prepared by methods known in the art, whereby the base may be reacted with an excess of the acid in a water immiscible solvent, such as ethylacetate as referred to above. Such citalopram salts as prepared by a process according to the present invention have high purity, substantially as hereinafter described in greater detail.

The present invention further provides use of at least one polybasic acid, either in free form or as a partial alkali metal salt, in the purification of citalopram, either in racemic or enantiomeric form. The preferred features of such a use as provided by the present invention are substantially as hereinbefore described with reference to a process as provided by the present invention. In particular, the present invention further provides use (i) of at least one polybasic acid, either in free form or as a partial alkali metal salt, so as to remove one or more citalopram impurities from a crude mixture including citalopram, either in racemic or enantiomeric form, wherein said citalopram impurities comprise one or more citalopram derivatives having higher basicity compared to citalopram; in combination with use (ii) of at least one polybasic acid, either in free form or as a partial alkali metal salt, so as to separate citalopram, either in racemic or enantiomeric form, from impurities remaining in the residual crude mixture obtained further to use (i), by extraction of citalopram, as a salt formed with the polybasic acid, into an aqueous phase.

In a further aspect the present invention provides citalopram free base, or a pharmaceutically acceptable salt thereof, either in racemic or enantiomeric form, prepared by a process according to the present invention substantially as hereinbefore described. Preferably, citalopram as prepared by a process according to the present invention includes less than about 0.1% of each of the above mentioned citalopram impurities. More particularly, citalopram as prepared by a process according to the present invention is suitably more than 99.7% w/w pure (peak area).

The term "crude mixture" as referred to herein refers to a mixture including citalopram impurities, which must be removed or which it is desired to remove. The term "citalopram impurities" as used herein includes citalopram derivatives substantially as hereinbefore described by name and structure. The crude mixture comprising citalopram base may be obtained directly from the synthesis of the citalopram by techniques known in the art, for Example by ring closure of 4-[4-(dimethylamino)-1-(4'-fluorophenyl)-1-hydroxybutyl]-3-(hydroxymethyl)-benzonitrile, or by conversion of 1-(4'-flurophenyl)-5-bromo pthalane to the corresponding cyano derivative, namely citalopram.

The present invention further provides, therefore, a process of preparing citalopram, either in racemic or enantiomeric form, by ring closure of 4-[4-(dimethylamino)-1-(4'-fluorophenyl)-1-hydroxybutyl]-3(hydroxymethyl)-benzonitrile, dissolving the resulting citalopram, together with one or more citalopram derivatives which are present as citalopram impurities, in a water immiscible organic solvent so as to provide a crude mixture thereof, and subjecting the resulting crude mixture to a purification process as provided by the present invention substantially as hereinbefore described.

The present invention further provides, therefore, a process of preparing citalopram, either in racemic or enantiomeric form, by conversion of 1-[3-(dimethylamino)propyl]-1-(4-flurophenyl)-5-bromo pthalane to the corresponding cyano derivative, namely citalopram, dissolving the resulting citalopram, together with one or more citalopram derivatives which are present as citalopram impurities, in a water immiscible organic solvent so as to provide a crude mixture thereof, and subjecting the resulting crude mixture to a purification process as provided by the present invention substantially as hereinbefore described.

In yet another aspect of the present invention, there is provided by the present invention a pharmaceutical formulation comprising citalopram as prepared by the present invention, together with a pharmaceutically acceptable carrier or excipient therefor.

Preferably a formulation as provided by the present invention can be for oral administration. The pharmaceutical formulations of the invention may, however, be administered in any suitable way and in any suitable form, for example orally in the form of tablets, capsules, powders or syrups, or parenterally in the form of usual sterile solutions for injection.

The pharmaceutical formulations of the invention may be prepared by conventional methods in the art. For example, tablets may be prepared by mixing the active ingredient with ordinary adjuvants and/or diluents and subsequently compressing the mixture in a conventional tabletting machine. Examples of adjuvants or diluents can comprise: corn starch, potato starch, talcum, magnesium stearate, gelatine, lactose, gums, and the like. Any other adjuvant or additive colourings, aroma, preservatives or the like may also be used provided that they are compatible with the citalopram as provided by the present invention.

Solutions for injections may be prepared by dissolving citalopram as provided by the present invention and possible additives in a part of the solvent for injection, typically sterile water, adjusting the solution to the desired volume, sterilisation of the solution and filling in suitable ampoules or vials. Any suitable additive conventionally used in the art may be added, such as tonicity agents, preservatives, antioxidants and the like.

The present invention further provides citalopram as prepared by a process according to the present invention, for use in the manufacture of a medicament for the treatment of a disease state prevented, ameliorated or eliminated by the administration of a serotonin reuptake inhibitor as described herein.

The present invention also provides a method of treating a disease state prevented, ameliorated or eliminated by the administration of a serotonin reuptake inhibitor in a patient in need of such treatment, which method comprises administering to the patient an effective amount of citalopram as prepared by a process according to the present invention.

The present invention will now be further illustrated by the following Examples which do not limit the scope of the invention in any way.

EXAMPLE 1

50 gms of 4-[4-(dimethylamino)-1-(4'-fluorophenyl)-1-hydroxybutyl]-3(hydroxymethyl)-benzonitrile (cyano diol) was added to a mixture of 50 gm phosphoric acid and 150 gm water. The mixture was heated to 105° C. for 14 hours. The reaction mixture was cooled to 40° C. and diluted with 1000 ml water. The pH of the solution was adjusted to 8-10 with liquor ammonia and extracted with ethyl acetate. The ethyl acetate layer was washed with 50 ml of 5% disodium edetate solution twice to remove the carboxamide impurity (about 3%) and the cyano diol impurity (about 0.8%). The ethyl acetate layer was dried over sodium sulphate, treated with decolorizing charcoal and filtered. The solution was acidified to a pH between 3-3.5 with 48% aqueous hydrobromic acid. The precipitated product of citalopram hydrobromide was filtered. This product had a purity of greater than 99.85%.

EXAMPLE 2

(S)-4-[4-(dimethylamino)-1-(4'-fluorophenyl)-1-hydroxybutyl]-3-(hydroxymethyl)-benzonitrile (12 gm) was dissolved in methylene chloride (180 ml). The solution was cooled to 0° C. and triethyl amine (13.5 ml) added. Methane sulphonyl chloride (4.8 ml) was dissolved in methylene chloride (20 ml) and added slowly to the reaction mixture at 0° C. The reaction mixture was stirred for 2 hours at 5° C. Water was added and the organic layer was washed with water twice. The organic layer was washed with 1% disodium edetate solution (25 ml). The organic layer was then extracted four times with 5% disodium edetate solution (100 ml). The aqueous layer was then separated and washed with methylene chloride. The pH of the aqueous layer was readjusted to between 9-10 with 10% aqueous sodium hydroxide and extracted with ethyl acetate. The ethyl acetate layer was concentrated under vacuum to oil, acetone (60 ml) was added and oxalic acid dihydrate (2.6 gm) was added. The reaction mixture was stirred for one hour at 10° C. and filtered. The solids were dried. The product of escitalopram had a purity of greater than 99.75%.

EXAMPLE 3

50 gm of 1-[3-(dimethylamino)propyl]-1-(4-flurophenyl)-5-bromo pthalane (5-bromo citalopram) and 30 gm of cuprous cyanide were mixed and heated under a nitrogen atmosphere to 140° C. to 150° C. for 6 hours. When the reaction mixture showed starting material less than 5%, dimethyl formamide (50 ml) was added at 140° C.-150° C. and stirred for 5 minutes. The reaction mixture was cooled to 80° C. and 50% v/v ethylene diamine solution was added and stirred for 15 minutes. Toluene (200 ml) was charged and the reaction mixture was stirred for 10 minutes. The lower aqueous layer was separated and the toluene washed with ethylene diamine (50 ml) solution twice. The toluene layer was washed twice with 5% disodium edetate solution (100 ml).

The toluene layer was extracted with 1000 ml of 5% disodiumn edetate solution three times. The combined aqueous extracts were washed with toluene (200 ml) twice. The aqueous layer was made alkaline with 10% sodium hydroxide solution and extracted with ethyl acetate (500 ml). The ethyl acetate layer was dried over anhydrous sodium sulphate and made acidic with 48% aqueous hydrobromic acid. The mixture was stirred for one hour and filtered to give citalopram hydrobromide (20 gm) having purity greater than 99.80%.

EXAMPLE 4

| S. No | Ingredients | Strength | | | Qty (Kg) |
|---|---|---|---|---|---|
| | | 10 | 20 | 40 | |
| | | Qty (mg/tablet) | | | |
| 1* | Citalopram hydrobromide | 12.495 | 24.99 | 49.98 | 19.86705 |
| 2** | Mannitol USP | 34.255 | 68.51 | 137.02 | 54.46545 |
| 3 | Microcrystalline cellulose NF | 31.25 | 62.50 | 125.00 | 49.6875 |
| 4 | Croscarmellose sodium NF | 2.50 | 5.00 | 10.00 | 3.975 |
| | Binder: | | | | |
| 5 | Starch NF | 2.00 | 4.00 | 8.00 | 3.180 |
| 6 | Purified water USP | Qs | Qs | Qs | 55.00 |
| | Lubricant: | | | | |
| 7 | Magnesium stearate NF | 2.50 | 5.00 | 10.00 | 3.975 |
| | Total: | 85.00 | 170.00 | 340.00 | 135.15 |

-continued

| S. No | Ingredients | Strength | | | Qty (Kg) |
|---|---|---|---|---|---|
| | | 10 | 20 | 40 | |
| | | Qty (mg/tablet) | | | |
| | Film coating: | | | | |
| 8 | Opadry 04F58804 White | 2.00 | 4.00 | 8.00 | |
| 9 | Purified water | Qs | Qs | Qs | |
| | Tablet weight: | 87.00 | 174.00 | 348.00 | |

*Quantity of citalopram hydrobromide to be dispensed based on 100% assay value (on as such basis). Only where the assay value (calculated on as such basis) is less than 99.5%, then the quantity of citalopram hydrobromide is to be adjusted by mannitol in the formula.
**To be adjusted to keep the weight of the tablet constant.

Tablets containing the above ingredients were prepared by known techniques of sifting, mixing, granulation, milling, lubrication and compression, followed by film coating, to obtain desired tablet formulations as provided by the present invention.

EXAMPLE 5

| S. No | Ingredients | Strength | | | Qty (Kg) |
|---|---|---|---|---|---|
| | | 10 | 20 | 40 | |
| | | Qty (mg/tablet) | | | |
| 1* | Citalopram hydrobromide | 12.495 | 24.99 | 49.98 | 22.491 |
| 2 | Mannitol Ph. Eur | 22.00 | 44.00 | 88.00 | 39.60 |
| 3** | Mannitol Ph. Eur | 44.275 | 88.55 | 177.10 | 79.695 |
| 4 | Microcrystalline cellulose Ph. Eur | 8.9425 | 17.885 | 35.77 | 16.0965 |
| 5 | Colloidal anhydrous silica Ph Eur | 0.3125 | 0.625 | 1.25 | 0.5625 |
| | Lubricant | | | | |
| 6 | Magnesium stearate Ph. Eur | 1.975 | 3.95 | 7.90 | 3.555 |
| | Total: | 90.00 | 180.00 | 360.00 | 162.00 |
| | Film coating: | | | | |
| 7 | Hypromellose 6 cps Ph. Eur | 1.095 | 2.190 | 4.380 | — |
| 8 | Titanium dioxide Ph. Eur | 0.440 | 0.880 | 1.760 | — |
| 9 | Macrogol 6000 Ph. Eur | 0.265 | 0.530 | 1.060 | — |
| 10 | Purified water Ph. Eur | Qs | Qs | Qs | — |
| | Tablet weight: | 91.80 | 183.60 | 367.20 | — |

*Quantity of citalopram hydrobromide to be dispensed based on 100% assay value (on as such basis), difference in quantity of citalopram hydrobromide to be adjusted by mannitol in the formula.
**Quantity to be adjusted to keep the weight of the tablet constant.

Tablets containing the above ingredients were prepared by known techniques of sifting, mixing, granulation, lubrication and compression, followed by film coating, to obtain desired tablet formulations as provided by the present invention.

The invention claimed is:

1. A process of purifying citalopram, either in racemic or enantiomeric form, which process comprises:
   (i) providing a crude mixture comprising citalopram, either in racemic or enantiomeric form, dissolved in a water immiscible organic solvent, and which mixture also includes one or more citalopram derivatives which are present as citalopram impurities;
   (ii) washing said crude mixture with at least one dilute aqueous solution of a polybasic acid of editic acid, either in free form or as a partial alkali metal salt, so as to separate said citalopram from citalopram impurities present in said crude mixture, said solution having a strength in the range of 0.5% to 6%; and
   (iii) where required converting citalopram free base, separated from citalopram impurities further to step (ii), to a pharmaceutically acceptable salt.

2. A process according to claim 1, which comprises carrying out an initial washing of the crude mixture with at least one dilute aqueous solution of a the polybasic acid, either in free form or as a partial alkali metal salt, so as to remove citalopram impurities from the crude mixture, and subsequently washing the residual crude mixture with at least one further dilute aqueous solution of a polybasic acid of editic acid, either in free form or as a partial alkali metal salt, said further solution having a strength in the range of 4% to 25%, with the proviso that the strength is greater than the strength of the polybasic acid used in the initial washing step, so as to separate citalopram, either in racemic or enantiomeric form, from the impurities remaining in the crude mixture, by extraction of citalopram, as a salt formed with the polybasic acid, into an aqueous phase.

3. A process according to claim 2, wherein the impurities removed from the crude mixture by the initial washing with said at least one dilute aqueous solution of the polybasic acid have a basicity of greater than the basicity of citalopram.

4. A process according to claim 3, wherein the impurities remaining in the crude mixture further to the initial washing with said at least one dilute aqueous solution of said polybasic acid have a basicity of less than the basicity of citalopram.

5. A process according to claim 2, wherein a base is added to the aqueous phase containing citalopram as a salt of the polybasic acid, in an amount sufficient to liberate citalopram free base which is then extracted into an organic solvent.

6. A process of purifying citalopram, either in racemic or enantiomeric form, which process comprises:
   (i) providing a crude mixture comprising citalopram, either in racemic or enantiomeric form, dissolved in a water immiscible organic solvent, and which mixture also includes one or more citalopram derivatives which are present as citalopram impurities;
   (ii) washing said crude mixture with at least one dilute aqueous solution of a polybasic acid of editic acid, either in free form or as a partial alkali metal salt, so as to remove citalopram impurities from the crude mixture, said solution having a strength in the range of 0.5% to 6%;
   (iii) washing the residual crude mixture obtained further to step (ii) with at least one further dilute aqueous solution of a polybasic acid of editic acid, either in free form or as a partial alkali metal salt, said further solution having a strength in the range of 4% to 25% with the proviso that the strength is greater than the polybasic acid used in the washing of step (ii), so as to separate said citalopram from impurities remaining in said residual crude mixture, by extraction of citalopram, as a salt formed with the polybasic acid, into an aqueous phase and optionally washing the resulting aqueous phase with an organic solvent;

(iv) adding a base to the aqueous phase in an amount sufficient to liberate citalopram free base and extracting the liberated citalopram into an organic solvent;

(v) optionally re-extracting citalopram free base from the organic extract obtained further to step (iv) by washing with at least one further dilute aqueous solution of a polybasic acid of editic acid, either in free form or as a partial alkali metal salt, so as to extract citalopram, as a salt formed with the polybasic acid, into an aqueous phase and adding thereto a base in an amount sufficient to liberate citalopram free base and further extracting the liberated citalopram into an organic solvent; and (vi) where required converting the free base obtained further to step (iv) or (v) to a pharmaceutically acceptable salt thereof.

7. A process according to claim 1, wherein the water immiscible solvent employed in step (i) is selected from the group consisting of toluene, ethyl acetate, hexane and methylene dichioride.

8. A process according to claim 7, wherein the water immiscible solvent is toluene or ethyl acetate.

9. A process according to claim 1, wherein the polybasic acid is employed as a partial alkali metal salt.

10. A process according to claim 9, wherein the alkali metal salt is the sodium salt.

11. A process according to claim 10, wherein said alkali metal salt is employed as disodium edetate.

12. A process according to claim 6, wherein the initial washing of the crude mixture with said at least one dilute aqueous solution of said polybasic acid of step (ii) removes impurities from the crude mixture having higher basicity compared to citalopram.

13. A process according to claim 3, wherein the initial washing removes one or more of the following impurities if present in the crude mixture: 5- carboxamide citalopram, N-desmethyl citalopram, desfluoro citalopram, 4[4-(dimethylamino)-1-(4'-fluorophenyl)-1-hydroxybutyl]-3-(hydroxymethyl)-benzonitrile and/or 5-formyl citalopram.

14. A process according to claim 2, wherein the polybasic acid is employed as the salt, disodium edetate, and wherein subsequent washing separates citalopram from the residual crude mixture, whereby citalopram as a salt formed with disodium edetate is extracted into an aqueous phase.

15. A process according to claim 6, wherein the impurities remaining in the residual crude mixture subsequent to the initial washing have a basicity of less than citalopram.

16. A process according to claim 4, wherein the impurities remaining in the residual crude mixture subsequent to the initial washing are selected from the group consisting of descyano citalopram, 5-chloro citalopram and 5-bromo citalopram.

17. A process according to claim 2, wherein the subsequent washing is carried out at a temperature in the range of 40 to 80° C.

18. A process according to claim 5, wherein said base comprises an aqueous alkali metal hydroxide solution.

19. A process according to claim 18, wherein the base is aqueous sodium hydroxide or potassium hydroxide.

20. A process according to claim 5, wherein the liberated citalopram free base is extracted from the aqueous phase into ethyl acetate.

21. A process according to claim 1, which includes converting citalopram free base to a pharmaceutically acceptable salt of citalopram.

22. A process according to claim 21, wherein the pharmaceutically acceptable salt is selected from the group consisting of the hydrobromide, hydrochloride and oxalate.

23. A process of preparing citalopram, either in racemic or enantiomeric form, by ring closure of 4-[4-(dimethylamino)-1-(4'-fluorophenyl)-1-hydroxybutyl]-3(hydroxymethyl)-benzonitrile, dissolving the resulting citalopram, together with one or more citalopram derivatives which are present as citalopram impurities, in a water immiscible organic solvent so as to provide a crude mixture thereof, and subjecting the resulting crude mixture to a purification process according to claim 1.

24. A process of preparing citalopram, either in racemic or enantiomeric form, by conversion of 1-[3-(dimethylamino)propyl]-1-(4-flurophenyl)-5-bromo pthalane to the corresponding cyano derivative, namely citalopram, dissolving the resulting citalopram, together with one or more citalopram derivatives which are present as citalopram impurities, in a water immiscible organic solvent so as to provide a crude mixture thereof, and subjecting the resulting crude mixture to a purification process according to claim 1.

25. A process of claim 1 wherein said polybasic acid salt is disodium edetate.

26. The process of claim 2 wherein said at least one further dilute aqueous solution of a polybasic acid salt is an aqueous solution of disodium edetate.

27. The process of claim 6 wherein the polybasic acid salt of step (ii) is disodium edetate.

28. The process of claim 6 wherein the polybasic acid salt of step (iii) is disodium edetate.

29. The process of claim 6 wherein step (v) re-extracts citalopram free base from the organic extract by washing with at least one further dilute aqueous solution of a polybasic acid salt of disodium edetate.

* * * * *